United States Patent [19]

Phykitt

[11] Patent Number: 5,723,453
[45] Date of Patent: Mar. 3, 1998

[54] STABILIZED, WATER-SOLUBLE ASPIRIN COMPOSITION

[75] Inventor: Howard P. Phykitt, Wilson, N.C.

[73] Assignee: Health Corporation, Rocky Mount, N.C.

[21] Appl. No.: 557,726

[22] Filed: Nov. 13, 1995

[51] Int. Cl.$^6$ .................................................. A61K 31/60
[52] U.S. Cl. ........................... 514/165; 514/159; 424/44
[58] Field of Search ........................ 514/159, 165; 429/44

[56] References Cited

U.S. PATENT DOCUMENTS

| | | | |
|---|---|---|---|
| 2,297,599 | 9/1942 | Wilen | 424/466 |
| 3,105,792 | 10/1963 | White | 424/44 |
| 3,495,001 | 2/1970 | Leonards | 424/44 |
| 3,903,255 | 9/1975 | Gusman et al. | 424/44 |
| 4,687,662 | 8/1987 | Schobel | 424/44 |
| 4,704,269 | 11/1987 | Korab | 424/44 |
| 4,942,039 | 7/1990 | Duvall et al. | 424/466 |
| 5,157,030 | 10/1992 | Galat | 514/165 |

FOREIGN PATENT DOCUMENTS

| | | |
|---|---|---|
| 0203768 | 12/1986 | European Pat. Off. . |
| 1328591 | 8/1973 | France . |
| 2708853 | 2/1995 | France . |

*Primary Examiner*—C. Warren Ivy
*Assistant Examiner*—D. Margaret M. Mach
*Attorney, Agent, or Firm*—Steven J. Hultquist

[57] ABSTRACT

A stabilized, essentially sodium free, alkaline and aspirin combination compound which is readily soluble in a preselected fluid, which when dissolved forms potassium acetylsalicylate. Such alkaline and aspirin combination compound consisting essentially of aspirin, having a predetermined particle size. Such aspirin being present in the alkaline and aspirin combination compound generally within a range of between about 325.0 mg and about 1,000.0 mg per unit dose. A preselected alkaline compound is present in such alkaline and aspirin combination compound generally within a range of between about 250.0 mg and about 3,000.0 mg per unit dose. The preselected alkaline compound having a ph generally within a range of between about 8.0 and 10.0 and such preselected alkaline compound being present in this alkaline and aspirin combination compound in a molar amount which is greater than a molar amount required to neutralize the aspirin.

23 Claims, No Drawings

STABILIZED, WATER-SOLUBLE ASPIRIN COMPOSITION

CROSS REFERENCE TO RELATED APPLICATION

This application is closely related to my co-pending application titled, "METHOD FOR PREPARATION OF A POTASSIUM AND ASPIRIN COMBINATION COMPOUND" which is being filed concurrently herewith. The teachings of this co-pending application are incorporated herein by reference thereto.

FIELD OF THE INVENTION

The present invention relates, in general, to pain relieving and/or antacid type compounds and, more particularly, this invention relates to a new and improved alkaline and aspirin combination compound which when mixed together is readily soluble in a predetermined fluid, such as water, and when dissolved form potassium acetylsalicylate and, still more particularly, this invention relates to such an alkaline and aspirin combination compound which is faster acting than previously known and/or used aspirin compounds and that can be an effective antacid.

BACKGROUND OF THE INVENTION

Prior to the present invention, aspirin and the use thereof as a suitable treatment for the temporary relief of minor aches and pain has been well established for many years. In fact, aspirin is the most commonly used pain relief medication on the market.

Unfortunately, however, the aspirin products which are currently available on the market have very poor solubility in water or any other fluid suitable for human consumption. In addition, it is well known that aspirin is an acidic drug which can cause gastric distress. Such gastric distress is caused primarily because the aspirin particles do not dissolve and such particles attach to the walls of the stomach and/or intestines.

Equally well known today is the significant role which aspirin may have in the successful treatment and management of two of the most common major diseases that afflicts the world's population, i.e. arthritis and heart attacks. It has been demonstrated that aspirin is both an effective analgesic and anti-inflammatory agent.

In addition, aspirin's beneficial effect on the human immune system may make it a promising drug for possible use in the treatment of cancer, AIDS, cataracts, allergies and a number of other diseases in which the immune system is involved. These valuable pharmacological properties have made aspirin the most widely used drug in the world.

Nevertheless, it has been documented that aspirin does possess a number of undesirable side-effects, although the true severity of these side-effects has not been recognized until recently. For example, being a sparingly soluble substance (only 0.33 gm in 100 ml of water), the undissolved particles of aspirin will normally adhere to the gastrointestinal mucosa. Such adherence can cause lesions, gastric and duodenal ulcers and bleeding. These undesirable side-effects are usually persistent and cumulative and they occur in a number of patients in which aspirin is used as a therapy. Gastroscopic and clinical studies, which have been reported in numerous medical journals, confirm the topical nature of these detrimental side-effects.

The corrosive effects that aspirin may display on the gastrointestinal mucosa were recognized early in the history of aspirin therapy. Consequently, attempts to produce a soluble form of this drug have been made almost continuously since then. See, for example, U.S. Pat. No. 740,703 issued in 1903. These efforts were concentrated almost exclusively on the preparation of various soluble salts, lithium, sodium, potassium, calcium and magnesium as well as with organic amines and amino acids (lysine and ormthine).

The main disadvantages of these particular salt products was that, in contrast to the aspirin itself, they were not stable. Most of these salts will contain water of crystallization which produces an intramolecular hydrolysis that results in the splitting of the molecule into salicylic and acetic acids. However, the attempts which have been made to prevent this unwanted decomposition by removing the water and forming an anhydrous salt have resulted in hygroscopic products which are not only difficult to handle and expensive to produce, but require special expensive moisture-proof packaging of each individual dose.

The cost of such products was so high that they could not successfully compete with aspirin in the marketplace. In addition, the use of these prior art salt products will often involve the ingestion of undesirably high amounts of metallic elements.

More recently, attempts have been made to eliminate these disadvantages and detrimental side-effects by a more simple and generally less expensive means. Thus, aspirin tablets were coated with layers of buffering agents that are designed to neutralize the gastric acidity. Calcium carbonate, magnesium carbonate, magnesium hydroxide, sodium aluminum carbonate, sodium aluminum glycinate and the like, are thus in use in a number of commercial aspirin products.

Clinical studies show that these methods are not entirely effective, partly because it is not possible to coat an aspirin tablet with a sufficient amount of a buffering agent to totally neutralize the gastric acid. Even if it were possible to do so, there is an immediate natural response of the human body which may cause the production of more acid, often in larger amounts than originally present (acid rebound).

Even more importantly, however, is the fact that the use of such buffering agents does not prevent the detrimental insoluble particles of aspirin from adhering to the gastrointestinal mucosa and causing corrosion. Another known prior art method used in commercial tablets is to enteric-coat them. Such coating is designed to prevent the aspirin release in the stomach and to exert its effect in the intestine. This, however, simply results in shifting the focus of the undesirable side-effects from the stomach to the intestine.

As mentioned above, the manufacture of soluble salts of aspirin is highly complicated and quite costly. A typical example is the manufacture of the sodium salt of aspirin as disclosed in U.S. Pat. No. 3,985,792.

The first step of this patented process involves the reacting of aspirin with sodium bicarbonate in water, which forms a solution of the sodium salt. In the second step, this solution is treated with isopropanol and cooled to 5° C., which causes the crystallization of sodium acetylsalicylate dihydrate. The third step involves the filtration and washing of the dihydrate. In the fourth step, the dihydrate, which is unstable, is dehydrated as soon as possible in a vacuum dryer or in a current of dry, inert gas, such as nitrogen. The final product is hygroscopic and must be handled, stored and packaged in humidity-controlled rooms.

Finally, isopropanol which is used in large amounts (10 lbs. per lb. of product) must be separated from water and recovered by fractional distillation. This involved process is even further complicated by the fact that the aspirin is decomposed by water and by isopropanol, which affects the yield, the purity and the stability of the final product.

It is generally well recognized, in the drug art, that aspirin will readily react with sodium bicarbonate to form an aqueous solution of the sodium salt. Therefore, it would seem logical that the costly and complicated preparation of the sodium salt could be avoided by simply adding the aspirin to the sodium bicarbonate, in premeasured amounts corresponding to the desired dose, to a glass of water, stirring the mixture until the aspirin is dissolved and drinking the solution.

This method would provide an aspirin solution simply and inexpensively, which is free of corrosion-causing insoluble particles to patients on aspirin therapy. And, indeed, such products are commercially available, usually in the form of effervescent tablets containing a mixture of aspirin, sodium bicarbonate and citric acid.

The major drawback of these products is that in order to accomplish such dissolution, with respect to even the smallest adult dose of aspirin (325 mg. 5 grains), it was found necessary to use large amounts of sodium bicarbonate (1900 mg.), which represents a very large excess, since the theoretical amounts needed is on the order of 152 mg. Even allowing for the fact that some of the sodium bicarbonate may be neutralized by the citric acid, the amount of the bicarbonate present is still equivalent to nearly 40 moles when only one mole is required for the reaction.

Aspirin when used for chronic pain and arthritis is usually taken in dosages of two tablets at a time, 325 mg. each, six times a day. The use of these commercially available prior art effervescent aspirin tablets described above would, while giving particle-free solutions of aspirin, involve the ingestion of about 7,000 mg. of elemental sodium per day. This amount of sodium is considered medically detrimental to a person's health in general, but particularly to older patients, and patients with hypertension.

As a result, these products are used only for the relief of occasional minor pain or an upset stomach. They should never be used on a regular basis by patients with arthritis or those on restricted sodium diets.

In the laboratory, or during industrial manufacture, as was disclosed in U.S. Pat. No. 5,157,030, the amount of sodium bicarbonate used is 46.7 parts per 100 parts of aspirin, whereas in the soluble aspirin tablet as described above, the amount is 1.250 parts, or more than about 20 times larger. The primary reason why it is necessary to use such large detrimental amounts of sodium bicarbonate, in commercially available effervescent tablets, can generally be explained by the kinetics of the reaction involved.

In the preparation of sodium aspirin, whether in the laboratory or on an industrial scale, the amount of water used is as small as practically possible. Thus, for 100 parts of aspirin and 46.7 parts of sodium bicarbonate, the amount of water required is about 50 parts. Therefore, the amount of aspirin is about 50% of the total, the amount of the sodium bicarbonate is about 25% and the amount of water is 25% also.

The purpose of using such high concentrations is to utilize the equipment capacity to its maximum, to produce the maximum yield on crystallization and to use the smallest amount of the solvent. Also, the use of high concentrations causes the reaction to be completed in a shorter period of time, since the rate of a chemical reaction is proportional to the product of the concentrations of the reactants.

The concentration of both reactants varies constantly as the reaction proceeds. The initial concentration of aspirin is low because of its low solubility, whereas that of the more soluble sodium bicarbonate is about 33%.

The situation is quite different when the use of single doses by individual patients is considered. Aspirin tablets are generally taken with about a half-glass of water (about 100 to 120 ml or about 3½ to 4 oz.). While the concentration of aspirin is the same in any amount of water, its value being determined by its solubility in water (0.33%) and is thus constant. The concentration of sodium bicarbonate can be varied as desired within relatively wide limits. However, if one wishes to use it in equimolecular proportions, a 325 mg dose of aspirin will require 152 mg of sodium bicarbonate to produce a solution.

If this dose is taken in 100 ml of water, the concentration of sodium bicarbonate will be, initially, 0.152% and will decrease as the reaction progresses. Thus, concentration values in the laboratory or the plant, on the one hand, and in personal usage on the other hand, are 33% vs 0.15%.

In order to bring the rate of the reaction within more practical limits, and since it is not possible to increase the concentration of aspirin, the only alternative has been to increase the concentration of undesirable sodium well beyond the stoichiometric proportions. As pointed out, the sodium content of such soluble aspirin products is so high as to make them unsuitable for most of the major applications of aspirin in medicine.

The influence of sodium bicarbonate concentrations on it's rate of reaction with aspirin was determined by stirring 325 mg of aspirin with variable amounts of sodium bicarbonate in 100 ml of water and recording the time needed for the formation of a solution. Aspirin USP mesh #325 was used. This is the finest particle size available commercially (Monsanto, "micromized"). In order to simulate the conditions of practical use as closely as possible, the mixture was stirred by hand and with a teaspoon in an 8 oz glass.

In order to be of practical use to individual patients, a dose of a soluble aspirin product should dissolve in about half a glass of water (100–120 ml; 3½–4 oz), in a reasonably short time (less than 60 seconds), with stirring by hand with a spoon. As mentioned, this is achieved in commercial products by the use of a large excess of sodium bicarbonate. However, this results in the ingestion of excessive amounts of sodium if the product is to be used on a regular basis.

SUMMARY OF THE INVENTION

The present invention provides a stabilized, essentially sodium free, alkaline and aspirin combination compound which is readily soluble in a preselected fluid, which when dissolved readily forms potassium acetylsalicylate. Such alkaline and aspirin combination compound consists essentially of aspirin, having a predetermined particle size, present in the alkaline and aspirin combination compound generally within a range of between about 325.0 mg and about 1,000.0 mg per unit dose. A preselected alkaline compound is present in such alkaline and aspirin combination compound generally within a range of between about 250.0 mg and about 3,000.0 mg per unit dose. This preselected alkaline compound should have a ph generally within a range of between about 8.0 and 10.0 and such preselected alkaline compound being present in the alkaline and aspirin combination compound in a molar amount which is greater than a molar amount required to neutralize such aspirin.

OBJECTS OF THE INVENTION

It is, therefore, one of the primary objects of the present invention to provide an improved alkaline and aspirin combination compound which will enable such aspirin compound to be more widely used in the treatment of arthritis and to substantially reduce the incidence of heart attacks.

Another object of the present invention is to provide an improved alkaline and aspirin combination compound which is relatively stable over an extended shelf life of the product.

Still another object of the present invention is to provide an improved alkaline and aspirin combination compound which is substantially totally soluble in water.

Yet another object of the present invention is to provide an improved alkaline and aspirin combination compound which will not irritate the gastric system.

A further object of the present invention is to provide an improved alkaline and aspirin combination compound which does not contain a sodium compound.

An additional object of the present invention is to provide an improved alkaline and aspirin combination compound which can act as an antacid.

Still yet another object of the present invention is to provide an improved alkaline and aspirin combination compound which has the potential to reduce the incidence of heart attacks.

Yet still another object of the present invention is to provide an improved alkaline and aspirin combination compound which has the potential to reduce the incidence of strokes.

A still further object of the present invention is to provide an improved alkaline and aspirin combination compound which has the potential to substantially prevent osteoporosis.

It is an additional object of the present invention to provide an improved alkaline and aspirin combination compound which is relatively fast acting when compared to commonly used aspirin compounds.

Another object of the present invention to provide an improved alkaline and aspirin combination compound which is relatively easy to manufacture.

Still another object of the present invention to provide an improved alkaline and aspirin combination compound which is relatively inexpensive to produce.

A further object of the present invention to provide an improved alkaline and aspirin combination compound which does not require a surfactant but may include one if desired.

In addition to the several objects and advantages of the present invention which have been described in detail above, various others objects and advantages of the present invention will become more readily apparent to those persons skilled in the aspirin formulation art from the following more detailed description of such invention.

BRIEF DESCRIPTION OF A PRESENTLY PREFERRED AND VARIOUS ALTERNATIVE EMBODIMENTS OF THE INVENTION

The present invention provides a stabilized, essentially sodium free, alkaline and aspirin combination compound. This alkaline and aspirin combination compound is readily soluble in a preselected fluid. Such preselected fluid preferably being water. When such alkaline and aspirin combination compound is dissolved it readily forms potassium acetylsalicylate.

In the present invention, this alkaline and aspirin combination compound consists essentially of aspirin granules having a predetermined particle size. Such predetermined particle size of these aspirin granules is preferably USP-60 mesh or smaller. The aspirin granules are present in the invented alkaline and aspirin combination compound generally within a range of between about 325.0 mg and about 1,000.0 mg per unit dose. In the presently preferred embodiment of the invention, such aspirin granules will be present in such alkaline and aspirin combination compound in a range of between about 650.0 mg and about 1,000.0 mg per unit dose. For certain medical applications it is preferred that such aspirin granules be present in such alkaline and aspirin combination compound at about 1,000.0 mg per unit dose.

The stabilized, essentially sodium free, alkaline and aspirin combination compound further includes a preselected granular alkaline compound which is present in the alkaline and aspirin combination compound generally within a range of between about 250.0 mg and about 3,000.0 mg per unit dose. The preselected granular alkaline compound will exhibit a ph generally within a range of between about 8.0 and 10.0. Such preselected granular alkaline compound is present in the alkaline and aspirin combination compound in a molar amount which is greater than a molar amount required to neutralize such aspirin granules.

In the presently preferred embodiment of this invention, such preselected granular alkaline compound is potassium bicarbonate. Such potassium bicarbonate is present in the alkaline and aspirin combination compound in a range of between about 780.0 mg and about 2,500.0 mg per unit dose. For certain medical applications it is preferred that such potassium bicarbonate granules be present in such alkaline and aspirin combination compound at about 1,210.0 mg per unit dose. The presently preferred ph range for such preselected alkaline compound is in the range of between about 8.6 and about 9.4. The optimum ph of such preselected alkaline compound is between about 8.8 and about 9.0.

Alternatively, according to the present invention, such stabilized, essentially sodium free, alkaline and aspirin combination compound which is readily soluble in a preselected fluid to form potassium acetylsalicylate may further include a sweetening agent. Such sweetening agent may be present in such alkaline and aspirin combination compound generally within a range of between about 1,135.0 mg and about 5,000.0 mg per unit dose. In a presently preferred embodiment of such alkaline and aspirin combination compound, this sweetening agent is selected from the group consisting of sucrose, fructose, saccharin, aspartame, dextrose and various mixtures thereof. The most preferred sweetening agent being sucrose. It is also preferred that the sucrose be present in such alkaline and aspirin combination compound in a range of between about 1,000.0 mg and about 5,000.0 mg per unit dose.

Such stabilized, essentially sodium free, alkaline and aspirin combination compound which is readily soluble in a preselected fluid to form such potassium acetylsalicylate may also include a preselected flavoring compound. Such flavoring compound can be present in such alkaline and aspirin combination compound generally within a range of between about 10.0 mg and about 50.0 mg per unit dose. If provided such flavoring compound is selected from the group consisting of fruit flavors. Such fruit flavors are preferably selected from orange, lemon, lime, cherry and various mixtures thereof and, preferably, are present in such alkaline and aspirin combination compound in a range of between about 20.0 mg and about 40.0 mg per unit dose.

In a presently preferred embodiment of the instant invention, such stabilized, essentially sodium free, alkaline and aspirin combination compound which is readily soluble in a preselected fluid to form potassium acetylsalicylate further includes a preselected acidic compound. Such preselected acidic compound may be present in such alkaline and aspirin combination compound generally within a range of between about 15.0 mg and about 1,000.0 mg per unit dose. Preferably, the preselected acidic compound will be selected from the group consisting of citric acid, tartaric acid, maleic acid, ascorbic acid and various mixtures thereof. The most preferred acidic compound being citric acid.

It is also within the scope of the present invention to provide the stabilized, essentially sodium free, alkaline and aspirin combination compound which is readily soluble in a preselected fluid, to form potassium acetylsalicylate, with a preselected surfactant. Such surfactant may be present in such alkaline and aspirin combination compound in an amount of at least about 0.25 percent by weight. If used it is preferred that such surfactant be present in such alkaline and aspirin combination compound in an amount of at least about 0.5 percent by weight. Finally, the presently preferred surfactant will be selected from the group consisting of lecithin, polysorbate, glycerol monosterate, sodium alkyl sulfate (such as, EMPICOL), oxyethyleneoxypropylene polymers and various mixtures thereof.

While a presently preferred and various alternative embodiments of the invention have been described in detail above, various other adaptations and modifications of the invention can be made by persons who are skilled in the drug art without departing from either the spirit of the invention or the scope of the appended claims.

I claim:

1. A stabilized, essentially sodium-free aspirin composition which is readily soluble in a preselected fluid, said aspirin composition consisting essentially of:

(a) aspirin granules having a predetermined particle size, present in said aspirin composition generally within a range of between about 325.0 mg and about 1,000.0 mg per unit dose;

(b) granular potassium bicarbonate having an outer surface layer of potassium carbonate on granules thereof, present in said aspirin composition generally within a range of between about 250.0 mg and about 3,000.0 mg per unit dose, having a pH generally within a range of between about 8.0 and about 10.0 and being present in a molar amount which is greater than a molar amount required to neutralize said aspirin granules.

2. A composition according to claim 1, further including a sweetening agent present generally within a range of between about 1,135.0 mg and about 5,000.0 mg per unit dose.

3. A composition according to claim 1, further including a flavoring compound present generally within a range of between about 10.0 mg and about 50.0 mg per unit dose.

4. A composition according to claim 1, further including an acidic compound present generally within a range of between about 15.0 mg and about 1,000.0 mg per unit dose.

5. A composition according to claim 1, wherein said predetermined particle size of said aspirin granular is USP-60 mesh or smaller.

6. A composition according to claim 5, wherein said aspirin granules are present in a range of between about 650.0 mg and about 1,000.0 mg per unit dose.

7. A composition according to claim 1, wherein said granular potassium bicarbonate having an outer surface layer of potassium carbonate on granules thereof, is present in a range of between about 780.0 mg and about 2,500.0 mg per unit dose.

8. A composition according to claim 1, wherein said ph of said granular potassium bicarbonate having an outer surface layer of potassium carbonate on granules thereof, is in a range of between about 8.6 and about 9.4.

9. A composition according to claim 2, wherein said sweetening agent is selected from the group consisting of sucrose, fructose, saccharin, aspartame, dextrose and various mixtures thereof.

10. A composition according to claim 2, wherein said sweetening agent is sucrose.

11. A composition according to claim 10, wherein said sucrose is present in a range of between about 1,000.0 mg and about 5,000.0 mg per unit dose.

12. A composition according to claim 3, wherein said flavoring compound is selected from the group consisting of fruit flavors.

13. A composition according to claim 12, wherein said fruit flavors are selected from orange, lemon, lime, cherry and various mixtures thereof and are present in a range of between about 20.0 mg and about 50.0 mg per unit dose.

14. A composition according to claim 4, wherein said acidic compound is selected from the group consisting of citric acid, tartaric acid, maleic acid, ascorbic acid and various mixtures thereof.

15. A composition according to claim 14, wherein said acidic compound is citric acid.

16. A composition according to claim 1, further comprising a surfactant present in an amount of at least about 0.25 percent by weight of the composition.

17. A composition according to claim 16, wherein said surfactant is present in an amount of at least about 0.5 percent by weight of the composition.

18. A composition according to claim 16, wherein said surfactant comprises sodium alkyl sulfate.

19. A therapeutic aspirin-based composition comprising (i) granular aspirin and (ii) granular potassium bicarbonate having an outer surface layer of potassium carbonate on granules thereof.

20. A composition according to claim 19, further comprising citric acid.

21. A composition according to claim 19, further comprising sucrose.

22. A composition according to claim 19, further comprising water in an amount sufficient to dissolve the aspirin granules and granular potassium bicarbonate having an outer surface layer of potassium carbonate on granules thereof, and to form potassium acetylsalicylate.

23. A therapeutic aspirin-based composition for the treatment or prophylaxis of a disease state or condition ameliorated or prevented by aspirin, said composition comprising in unit-dose form:

(a) from about 325.0 mg to about 1,000.0 mg of granular aspirin;

(b) from about 780.0 mg to about 2,500.0 mg of granular potassium bicarbonate having an outer surface layer of potassium carbonate on granules thereof; and (c) from about 15.0 mg to about 1,000.0 mg of citric acid.

* * * * *